(12) United States Patent
Wang et al.

(10) Patent No.: US 8,378,089 B2
(45) Date of Patent: Feb. 19, 2013

(54) COMPOSITIONS FOR PROTECTION AND CELLULAR DELIVERY OF INTERFERING RNA

(75) Inventors: Kai Wang, Bellevue, WA (US); David Galas, Seattle, WA (US)

(73) Assignee: Institute for Systems Biology, Seattle, WA (US)

( * ) Notice: Subject to any disclaimer, the term of this patent is extended or adjusted under 35 U.S.C. 154(b) by 0 days.

(21) Appl. No.: 13/032,459

(22) Filed: Feb. 22, 2011

(65) Prior Publication Data

US 2011/0230425 A1    Sep. 22, 2011

Related U.S. Application Data

(60) Provisional application No. 61/306,864, filed on Feb. 22, 2010.

(51) Int. Cl.
*C07H 21/04* (2006.01)

(52) U.S. Cl. .................. 536/24.5; 536/24.31; 536/24.1; 514/44

(58) Field of Classification Search .................. None
See application file for complete search history.

(56) References Cited

PUBLICATIONS

Mukudai et al. (Molecular and Cellular Biology 2008, vol. 28(19): 6134-6147).*
Leask, J. Cell Commun. Signal (2009) 3:85-86.
Nawa et al., J. Leukoc. Biol. (2009) 86(3):645-653.
Wang et al., Nucleic Acids Research (2010) 38(20):7248-7259.

* cited by examiner

*Primary Examiner* — Kimberly Chong
(74) *Attorney, Agent, or Firm* — Morrison & Foerster LLP

(57) ABSTRACT

Compositions and methods for protecting and administering small RNA to preserve stability are described. The small RNAs may either be in unmodified form or may be chemically modified to enhance stability further.

18 Claims, 2 Drawing Sheets

COMPOSITIONS FOR PROTECTION AND CELLULAR DELIVERY OF INTERFERING RNA

RELATED APPLICATION

This application claims priority from provisional application U.S. Ser. No. 61/306,864 filed 22 Feb. 2010. The contents of this document are incorporated herein by reference.

ACKNOWLEDGEMENT OF GOVERNMENT SUPPORT

The invention was supported in part by the National Science Foundation (FIBR Grant EF0527023 and by the Department of Defense. The U.S. Government has certain rights in this invention.

TECHNICAL FIELD

The field of the invention is in RNA protection strategies, including protection in drug delivery formulations. This invention includes compositions for delivery of interfering RNA molecules that comprise complexes of said RNA with the RNA protective protein NPM1. The complexation protects the RNA molecules from degradation.

BACKGROUND ART

MicroRNAs (miRNA) are endogenously produced small non-coding regulatory RNA molecules. Through sequence complementation, miRNA interacts with specific messenger RNAs (mRNAs) and affects the stability of mRNAs and/or the progression of protein translation. It has been estimated that over 30% of mRNAs are regulated by miRNA. siRNA is a synthetic molecule, usually consisting of double-stranded RNA with short single-stranded ends, which is transfected into cells and binds to RISC. siRNA is perfectly complementary to a particular target mRNA and cleaves that target. siRNA also suppresses translation of many off-target mRNAs that have partial sequence complementarity. Because of their ability to regulate protein production, these small RNAs are being developed as therapeutics.

A significant number of microRNAs have been observed in the extracellular space. These extracellular miRNAs are stable and the changes in their spectrum have been demonstrated as sensitive and informative biomarkers for specific disease conditions. The existence of stable extracellular microRNAs also suggests the possibility of microRNA as one of the mediators involved in the cell-cell communication. In any event, the stability of microRNA in the extracellular space suggests a mechanism is available for stabilizing these inherently unstable molecules.

One possibility for such stabilization is complexation with proteins that are known to bind RNA. A number of such proteins are known; however, these have not been shown to protect RNA from degradation, and indeed, as shown below, not all RNA binding proteins are protective.

In addition to microRNAs as therapeutics, these molecules may be therapeutic targets as well. One possibility for attacking such targets is the use of small RNA complementary to miRNAs. For example, the mir122 miRNA, which is liver specific, is required for the replication of Hepatitis C virus. This is just one example of abnormal miRNA expression that is associated with disease where the pathogens can use pathogen-encoded miRNAs or utilize host miRNAs to modulate responses to the pathogens that benefit the pathogens themselves.

One of the major obstacles to use of small RNA including miRNA or siRNA as a therapeutic is the difficulty in delivery of stable RNA molecules into the body. In one approach, various chemical modifications of the nucleotide structures have been developed to prevent RNAse degradation and enhance stability. These modifications change the nature of the molecules and thus may affect the specific interaction with its intended target molecules and cause unpredictable adverse effects. Further, even though chemically modified RNA molecules are relatively stable in circulation, significant amounts are required to obtain the intended biological effects. Such high concentrations may generate immune responses preventing additional treatment based on similar molecules. In addition, the pharmacodynamic and pharmacokinetic properties of each of these modified RNA molecules need to be extensively investigated due to the unpredictable properties of adsorption, distribution, metabolism and excretion (ADME).

As noted above, a number of RNA binding proteins are known. It has been suggested that one of these NPM1 may be involved in shuttling RNAs and ribosomal proteins to the cytosol (Leask, A., *J. Cell Commun. Signal* (2009) 3:85-86) and in a recent report it has also been identified outside the cell (Nawa, Y., et al., *J. Leukoc. Biol.* (2009) 86:1-9).

DISCLOSURE OF THE INVENTION

An RNA binding protein, nucleophosmin (NPM1) that is involved in the transportation and stabilization of extracellular (exported) miRNAs is disclosed herein. The activity of this protein as interacting with microRNA and protecting it from degradation has not been reported.

Using synthetic mir-122 RNA, we have discovered NPM1 among the RNA binding proteins we have tested can interact with small RNA to protect it from RNAse degradation thus providing a means to use small RNA as a therapeutic with the advantages of more reliable target interaction and predictable pharmacokinetic and pharmacodynamic properties. In addition, the RNA-protecting protein NPM1 may also stabilize chemically modified RNA molecules so as to reduce the concentration required for specific therapeutic effects.

Thus, in one aspect, the invention is directed to an isolated composition comprising a complex of small RNA molecules with the RNA protective protein NPM1. The invention also relates to methods to protect small RNA molecules from degradation by complexing them with NMP1.

In another aspect, the invention is directed to a pharmaceutical or veterinary composition which comprises small RNA molecules complexed with the protective RNA binding NPM1 protein and a pharmaceutically acceptable carrier. The small RNA may be unmodified or chemically modified for further stability.

In another aspect, the invention is directed to a method to deliver a small RNA based therapeutic or prophylactic by contacting cells with said pharmaceutical composition, including administering said pharmaceutical or veterinary composition to a subject comprising said target cells.

MODES OF CARRYING OUT THE INVENTION

Figure 1:
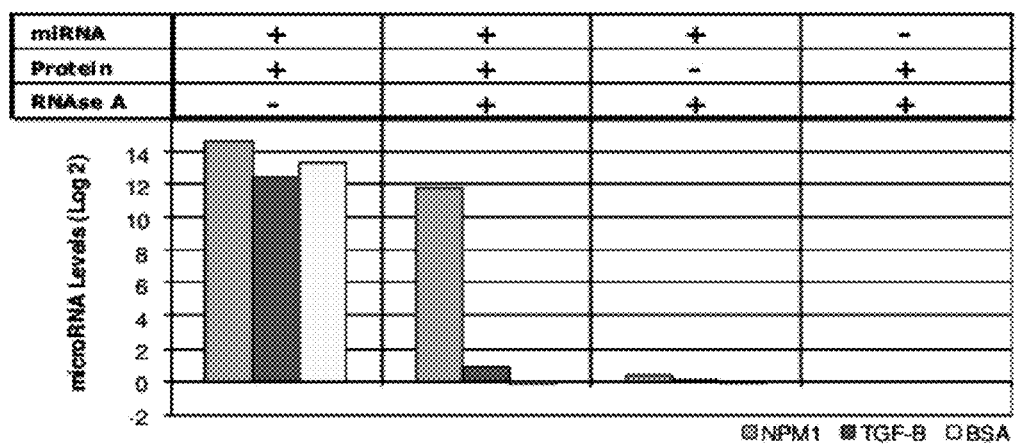
FIG. 1 is a graph showing the ability of NPM1 to protect miRNA from RNAse degradation.

The invention resides in the discovery that the RNA binding protein NPM1 found in extracellular space is able to protect miRNA molecules from degradation by RNAse. This is illustrated in the examples below. Discovery of the protective effect of this protein permits design of compositions for protection of small RNAs in general including pharmaceutical and veterinary compositions.

All of the compositions of the invention are "isolated" in a sense that they do not occur in any natural environment. They may, for example, consist of a fractionated portion of culture medium or be of a further purified form of the complex or the complex may be formed by the practitioner by combining the NMP1 with short RNA. Such compositions are useful in a number of contexts, including laboratory models of disease and experimental work with cell cultures. The compositions of the invention may also pharmaceutical or veterinary compositions. These compositions are useful for administering short RNA for therapeutic and prophylactic purposes.

As used herein, "small RNA" or "short RNA" refers to a short (20-30 nucleotides) single-stranded or double-stranded RNA, including miRNA and siRNA. Small RNA useful in medicine and in laboratory studies is sufficiently able to base pair with a desired target messenger RNA to interrupt translation and reduce the production levels of protein encoded by said messenger RNA. The small RNA may also be complementary to an undesired target miRNA. The small RNA may be unmodified or may contain chemical modifications such as phosphorothioate or phosphoroamidate linkages further to enhance stability.

While siRNA and miRNA are generally synthetic vs endogenous counterparts, siRNA is typically prepared to have complete complementarity to a target sequence, while endogenously produced miRNA does not share this feature. miRNA is transcribed from a non-coding region of the genome and is sufficiently homologous to a number of targets to effect silencing. The small RNA contained in the compositions of the invention useful in treatment or prophylaxis may have either feature—the degree of complementarity will depend on the design of the particular small RNA molecule. The small RNA useful in the invention contains 20-30 nucleotides per strand, and is sufficiently similar to a target to be effective in silencing. The small RNA is typically but not necessarily double stranded with the possibility of short overhangs.

The examples below demonstrate that NPM1 is effective in stabilizing synthetic miRNA by forming complexes therewith. Complexes with small RNA are readily formed simply by mixing the desired small RNA with NPM1. If desired, the ability of the complex to resist degradation by RNase can be demonstrated using art-known procedures. In any event, the complex is then included in a suitable composition, and, if desired, along with a pharmaceutically acceptable carrier.

Subjects suitable for treatment using the compositions of the invention are typically human or veterinary subjects. Veterinary subjects may be mammals, such as horses, cats, dogs, pigs, bovines, sheep, and the like, or may be avian subjects such as poultry.

Pharmaceutically acceptable carriers are well known in the art, and a compendium of these carriers is set forth in *Remington's Pharmaceutical Sciences*, latest edition, Mack Publishing Co., Easton, Pa., incorporated herein by reference. Included among such carriers are buffers, stabilizers, fillers, antioxidants, and other excipients that facilitate administration. The carriers may result in formulations that are, for example, liquid, including emulsions, or solid, including gels, powders or pastes. Additional pharmaceutical carriers include particulate carriers such as liposomes, micelles, block copolymer micelles, nanoparticles, such as fluorocarbon nanoparticles or polymer-lipid hybrid systems. These are merely exemplary and do not represent an exhaustive list. The nature of the pharmaceutical carrier, which makes up the pharmaceutical or veterinary composition will depend on the circumstances under which administration will occur.

Dosage levels, too, will depend on the nature of the subject to be treated, the nature of the target, and the mode of administration.

The compositions can be administered by any suitable means including parenteral or oral administration. The composition may be administered parenterally by intraarterial, intravenous, intraperitoneal, subcutaneous or intramuscular injection either continuously or by bolus injection, depending on the route of administration. The administration may also be transmembrane or transmucosal using suppositories and, optionally, agents to aid penetration of membranes or mucosal membranes. Topical administration and direct administration to a target area may also be performed.

Thus, the complexes of the invention may employ any conventional administration technique and any conventional pharmaceutically acceptable carrier.

The invention is not limited solely to pharmaceutical or veterinary applications, however. Generally, the invention is directed to methods to protect short RNA from degradation by contacting the short RNA with NPM1 so as to form a protected complex. Compositions purely for this purpose are simply isolated compositions containing the complex.

As used herein, "a", "an" and the like are intended to included both singular and plural interpretations. In addition, any documents cited herein are incorporated by reference.

The following examples are intended to illustrate but not limit the invention.

EXAMPLE 1

Short RNA Protection by NPM1 Protein

Synthetic microRNA mir-122 (100 pmole) was mixed with different proteins, NPM1 (3 pmole), TGF beta (4 pmole) or BSA (1.5 nmole) for 30 minutes followed by adding RNAse A (7 nmole) for another 30 minutes' incubation at 37° C., with the results shown in FIG. 1. Various control experiments by omitting RNAse A, protein, or microRNA were also included, as indicated on top of the figure. The miRNA levels from each condition were determined and normalized against no miRNA control.

As shown in FIG. 1, NPM1 is highly effective in protecting the small RNA while control proteins are not.

Figure 2:
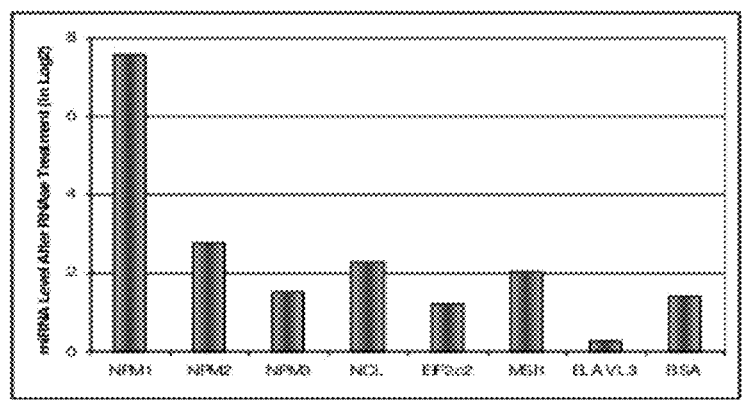
FIG. 2 is a graph showing comparative ability of several known RNA binding proteins to protect miRNA from RNase degradation. It will be seen that NPM1 is singularly effective.

However, as shown in FIG. 2, not all proteins that are known to bind to RNA successfully protect miRNA from degradation. Synthetic microRNA mir-122 (100 pmole) was mixed with 3 pmol of different RNA binding proteins as indicated on the X-axis for 30 minutes followed by adding RNAse A (7 nmole) for another 30 minutes' incubation at 37° C. BSA (1.5 nmole) was used as negative control for the experiment. Control experiments by omitting RNA binding protein were also included. The relative levels of miRNA after RNAase A treatment compared to such treatment no RNA binding protein are displayed. Clearly, NPM1 alone is unique in its ability to protect RNA, although the remaining tested proteins other than BSA are known to bind RNA.

EXAMPLE 2

Correlation of Exported miRNA Content with RNA Binding Protein NPM1

The present inventors have demonstrated that miRNAs are exported into the cell culture medium upon serum deprivation. Lysis of the cells was shown to be absent by demonstrating that the lactate hydrogenase (LDH) levels in serum-free media show no significant changes during the experimental period, up to 48 hours after serum depletion. It was demonstrated that two different cell lines A549 (lung epithelial carcinoma) and HepG2 (hepatocellular carcinoma) secreted miRNA into the medium upon serum depletion. Pertinent to the invention herein, the fractionated medium after serum depletion demonstrates that the presence of miRNA of various species correlates with the presence of NPM1 protein.

The inventors have also tested medium from primary human pulmonary fibroblast cells obtained from a Siencell Research Laboratories (Carlsbad, Calif.), grown in fibroblast medium on collagen 1-coated culture flasks and subjected to serum depletion by mass spectra techniques.

Cells were grown as above and the serum free medium was concentrated using Amicon Ultra Centrifugal Filter Devices (Millipore, Billerico, Mass.). The concentrated medium was enzymatically digested with trypsin and desalted with C18 Ultramicrospin columns (The Nest Group, Southborough, Mass.). After drying in a Savant speedvac (Thermo Scientific, Waltham, Mass.) the sample was re-suspended and run on Q-TOF Ultima API Mass Spectrometer (Waters, Bedford, Mass.). The results were analyzed using SEQUEST (v.27) against a human International Protein Index (IPI) database (v.3.38). This analysis showed the presence of 179 protein. These proteins included 12 proteins that are known to bind RNA, including NPM1, as shown in Table 1 below.

As shown in Table 1 the proteins listed are highly represented in the extracellular space in cells secreting miRNA. Not all of these proteins, however, are useful in the methods of the invention as agents for complexation to stabilize small RNA present therein.

TABLE 1

| Gene Symbol | Number of peptides observed | Gene Name |
|---|---|---|
| HNRNPA2B1 | 2 | heterogeneous nuclear ribonucleoprotein a2/b1 |
| HNRPAB | 3 | heterogeneous nuclear ribonucleoprotein a/b |
| ILF2 | 2 | interleukin enhancer binding factor 2, 45 kda |
| NCL | 7 | nucleolin |
| NPM1 | 4 | nucleophosmin (nucleolar phosphoprotein b23, numatrin) |
| RPL10A | 2 | ribosomal protein 110a |
| RPL5 | 2 | ribosomal protein 15 |
| RPLP1 | 6 | ribosomal protein, large, p1 |
| RPS12 | 2 | ribosomal protein s12 |
| RPS19 | 2 | ribosomal protein s19 |
| SNRPG | 2 | small nuclear ribonucleoprotein polypeptide g |
| TROVE2 | 2 | trove domain family, member 2 |

In the experiment below, medium from cells exporting miRNA was fractionated and the fractions assayed for miRNA and protein.

HepG2 cells were obtained from American Type Culture Collection (ATCC, Manassas, Va.) and grown in recommended medium containing 10% fetal bovine serum (FBS), 100 U/ml penicillin and 100 µg/ml streptomycin (Invitrogen, Carlsbad, Calif.) at 37° C. under 5% $CO_2$. This strain of HepG2 does not express CYP2E1. For serum depletion experiments, the cells were inoculated and grown for 24 hours with 10% FBS-containing media prior to switching to serum-free media. Serum free medium contained the basic medium as provided by Invitrogen (Carlsbad, Calif.) with 100U/ml penicillin and 100 µg/ml streptomycin.

To measure miRNA, QRT-PCR combined with microarray analysis was used in either order. For quantitative PCR, cDNA was generated using the miScript Reverse Transcription kit (Qiagen, Germantown, Md.). In brief, miRNAs were polyadenylated by using poly(A) polymerase and cDNA was generated with reverse transcriptase using a tag containing oligo-dT primers. The tag on oligo-dT served as universal primer in QPCR step.

Human miScript Assay 384 set v10.1 (Qiagen, Germantown, Md.) was used for real-time PCR analysis. To reduce pipetting error, the Matrix Hydra eDrop (Thermo Scientific, Hudson, N.H.) was used to mix the cDNA sample and qPCR master reagent. The data were analyzed by SDS Enterprise Database 2.3 (Applied Biosystems, Foster City, Calif.).

miRNA microarrays were performed using the manufacturer's (Agilent, Santa Clara, Calif.) protocol. 100 ng of total RNA was dephosphorylated with calf intestinal alkaline phosphate, and denatured with heat in the presence of dimethyl sulfoxide (DMSO). T4 RNA ligase added the Cyanine 3-cytidine biphosphate (pCp) to the dephosphorylated single stranded RNA. MicroBioSpin 6 columns (Bio-Rad, Hercules, Calif.) were used to remove any unincorporated cyanine dye from the samples. The purified labeled miRNA probes were hybridized to human miRNA V2 oligo microarrays in a rotating hybridization oven at 10 rpm for 20 h at 55° C. After hybridization, the arrays were washed in Agilent GE Wash Buffer 1 and 2 with Triton X-102. Then the array slides were dried immediately by a nitrogen stream and scanned at 5-um resolution by using a PerkinElmer ScanArray Express array scanner.

For fractionation, the serum free media were collected and centrifuged at 1000×g for 10 minutes to remove cell debris. This supernatant (25 ml) was transferred to a new tube and spun at 16K×g for 60 minutes, the pellet microvesicles, were washed and resuspended in phosphate-buffered saline (PBS, 137 mM NaCl, 2.7 mM KCl, 10 mM Sodium Phosphate dibasic, 2 mM Potassium Phosphate monobasic at pH of 7.4). The supernant of the 16K×g spun was transferred to a new tube and further centrifuged at 120K×g for 60 minutes to pellet the exosome particles. The exosome depleted supernatant was then spun at 220K×g for 60 minutes. The final supernatant was concentrated using Amicon Ultra Centrifugal Filter Devices (Millipore, Billerico, Mass.) to a final volume of 0.5 ml. The pellets, microvesicles, exosomes, and 220K×g pellet were resuspended in 0.5 ml PBS, so that the total volume of medium contributing to each was identical.

The resulting fractions were, then, a 16.5K Pellet which contains microvesicles; a 120K Pellet which contains the exosome fraction, a 220K Pellet, and the supernatant from the 220K Pellet.

Figure 3:
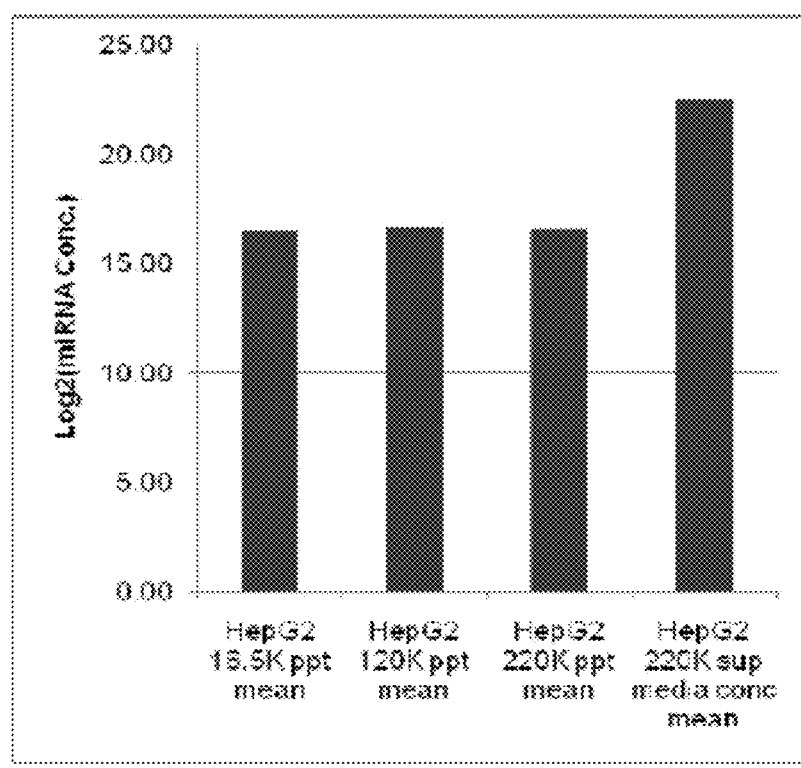
FIG. 3 is shows the average levels of miRNA in various fractions obtained from HepG2 cells after two hours of serum deprivation.

The distribution profile for various miRNAs from the serum deprived HepG2 cells is shown in FIG. 3. As is apparent, the predominant fraction containing high levels of miRNA is the 220K supernatant. This was then correlated with the presence of NPM1.

To measure protein concentrated medium and pellet samples were separated by sodium dodecyl sulfatepolyacrylamide gel electrophoresis (SDS-PAGE). The proteins were transferred to a nitrocellulose membrane (Bio-Rad, Hercules, Calif.). Human NPM1 was detected on the western blot blocked with 5% nonfat dry milk using an anti-NPM1 monoclonal antibody (Sigma, St. Louis, Mo.). Near-infrared (NIR) IRDye 680 labeled secondary antibodies (Li-Cor, Lincoln, Nebr.) were used to visualize the NPM1 antibody. The membrane was scanned using the Odyssey infrared imaging system (Li-Cor, Lincoln, Nebr.).

Western blot of the various fractions demonstrated that NPM1 was essentially exclusively present in the 220K supernatant fraction, correlating its presence with its presence of miRNAs.

The invention claimed is:

1. An isolated composition which comprises a complex of single-stranded or double-stranded small RNA and the RNA protective protein NPM1, wherein said small RNA consists of 20-30 nucleotides per strand.

2. The composition of claim 1, which is a pharmaceutical or veterinary composition and said complex is in admixture with an acceptable carrier.

3. The composition of claim 1, wherein the small RNA is not chemically modified.

4. The composition of claim 2, wherein the small RNA is not chemically modified.

5. The composition of claim 1, wherein the small RNA is siRNA or miRNA.

6. The composition of claim 2, wherein the small RNA is siRNA or miRNA.

7. The composition of claim 1, wherein the small RNA is double stranded.

8. The composition of claim 2, wherein the small RNA is double stranded.

9. The composition of claim 2, which is in the form of a tablet, capsule, syrup, paste or powder.

10. The composition of claim 2, which is in a form for parenteral administration and contained in a syringe or an IV administration container.

11. A method to administer small RNA to a cell which method comprises contacting a cell to be treated with said small RNA with the composition of claim 1.

12. A method to administer small RNA to a cell which method comprises contacting a cell to be treated with said small RNA with the composition of claim 2.

13. The method of claim 12, wherein said cell is contained in a subject, and said contacting comprises administering said composition to the subject.

14. The method of claim 13, wherein the subject is human.

15. A method to protect small RNA from degradation which comprises contacting the small RNA of claim 1 with the RNA protective protein NPM1.

16. The method of claim 15 wherein the small RNA is not chemically modified.

17. The method of claim 15 wherein the small RNA is siRNA or miRNA.

18. The method of claim 15 wherein the small RNA is double stranded.

* * * * *